(12) United States Patent
Stobie

(10) Patent No.: US 6,383,147 B1
(45) Date of Patent: May 7, 2002

(54) ANATOMICAL ORIFICE SIZERS AND METHODS OF ORIFICE SIZING

(75) Inventor: Robert Stobie, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 09/491,987

(22) Filed: Jan. 26, 2000

Related U.S. Application Data
(60) Provisional application No. 60/117,258, filed on Jan. 26, 1999.

(51) Int. Cl.$^7$ .................................................. A61B 5/00
(52) U.S. Cl. ........................ 600/587; 623/2.1; 128/898
(58) Field of Search ................................ 623/2.11, 2.1; 702/41, 104, 133, 139; 73/1.15, 865, 432.1; 604/338; 600/432, 587; 128/898; 607/17

(56) References Cited

U.S. PATENT DOCUMENTS

| | | | |
|---|---|---|---|
| 4,211,241 A | | 7/1980 | Kaster et al. |
| 5,042,161 A | | 8/1991 | Hodge |
| 5,360,014 A | | 11/1994 | Sauter et al. |
| 5,489,296 A | * | 2/1996 | Love et al. ............. 623/2 |
| 5,531,785 A | | 7/1996 | Love et al. |
| 5,545,214 A | * | 8/1996 | Stevens ............... 623/2 |
| 5,814,098 A | | 9/1998 | Hinnenkamp et al. |
| 6,045,576 A | * | 4/2000 | Starr et al. ............. 623/2 |

FOREIGN PATENT DOCUMENTS

| | | |
|---|---|---|
| GB | 2083362 | 3/1982 |
| WO | WO 97/25003 | 7/1997 |
| WO | WO-97/25003 | * 7/1997 ............. A61F/2/24 |

OTHER PUBLICATIONS

Booklet entitled "Carpentier–Edwards® Pericardial Bioprostheses Mini–Symposium", Chicago, IL, Baxter Healthcare Corporation, Edwards CVS Division, Apr. 24, 1993; pp. 51–62, "Sizing and Implantation".
Brochure entitled "Judge Our Pericardila Valve by its Appearance and You Will Only Get Half the Picture", Edwards CVS Division, Baxter Healthcare Corporation, 1969.

* cited by examiner

*Primary Examiner*—Dinh X. Nguyen
*Assistant Examiner*—Urmi Chattopadhyay
(74) *Attorney, Agent, or Firm*—Debra D. Condino; John Christopher James; Guy L. Cumberbatch

(57) ABSTRACT

Anatomical orifice sizers that are optimally proportional to an associated prosthetic device such as a heart valve, and methods of use are provided. The sizers are desirably slightly larger than the rigid mounting diameter of the corresponding heart valve. The heart valve sizer may be cylindrical and have a diameter about 0.3 mm larger than the valve mounting diameter. The sizer preferably has a length of between about 19 mm to 22 mm, and the edges are desirably rounded to a minimum 1 mm radius. The method includes providing a set of cylindrical sizers having varying diameters; sequentially inserting at least two of the sizers through the annulus; measuring the push force needed to pass each sizer through the annulus; selecting a valve corresponding to the sizer for which the measured push force is between about 150 and 300 grams.

2 Claims, 9 Drawing Sheets

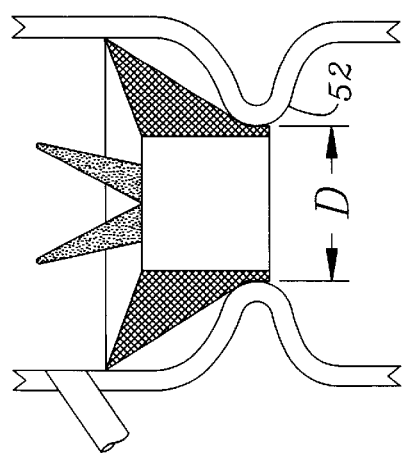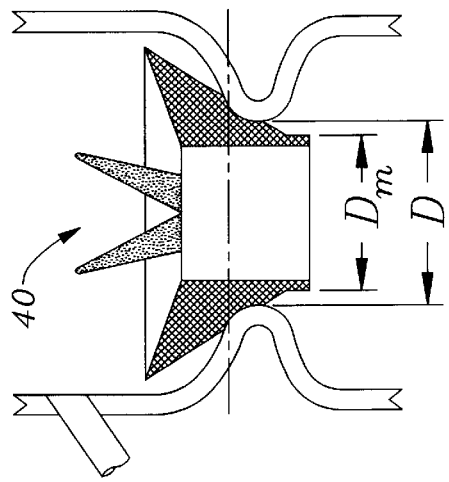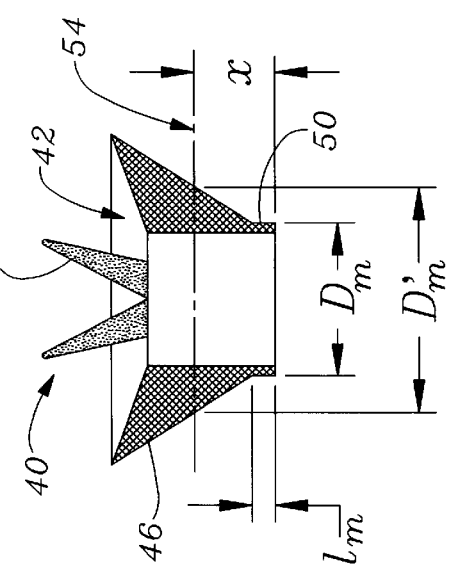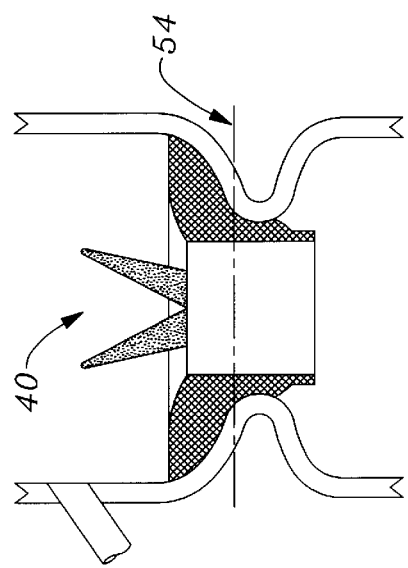

Fig. 6
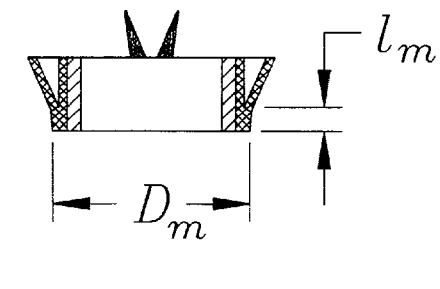
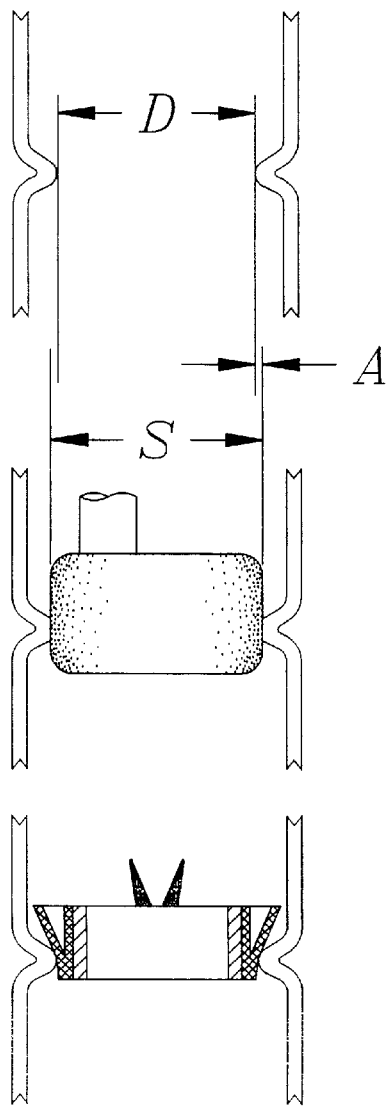
Fig. 7
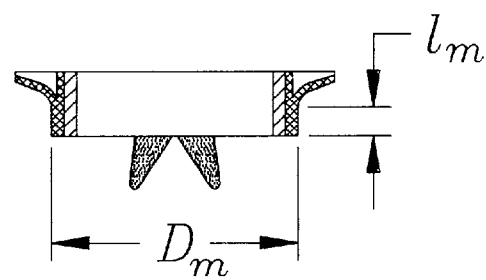
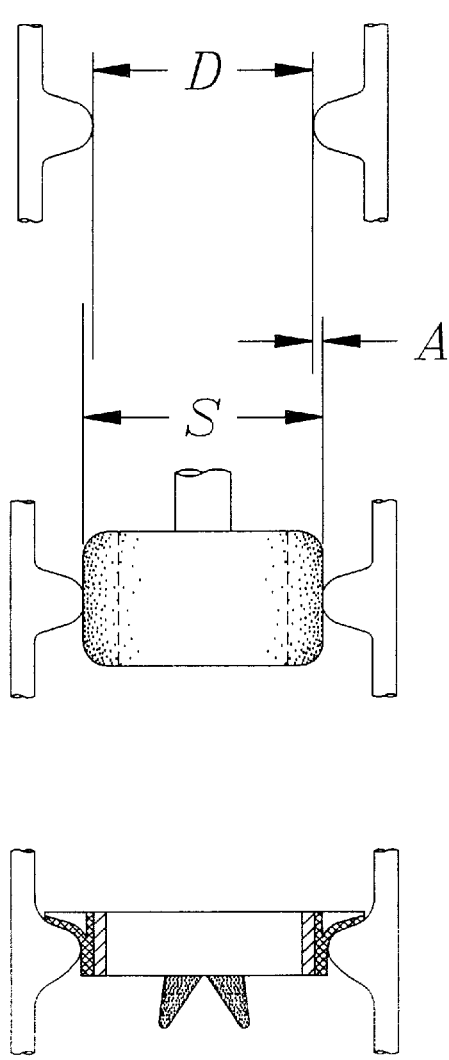

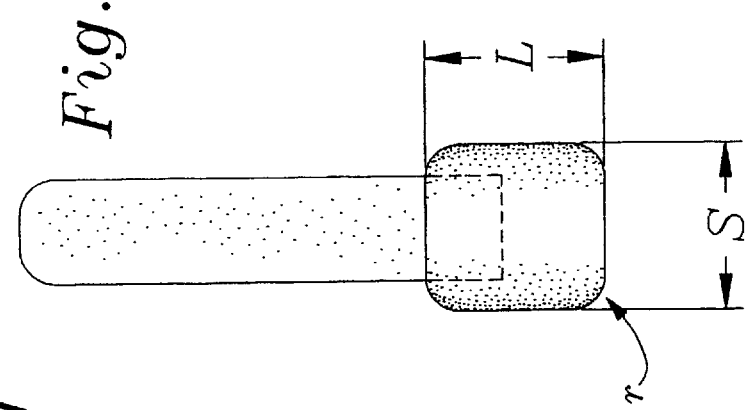
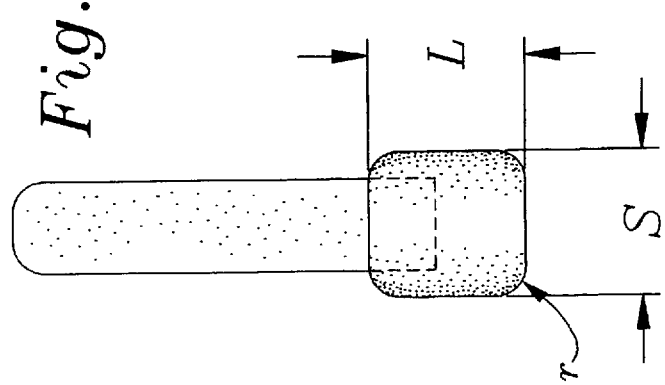
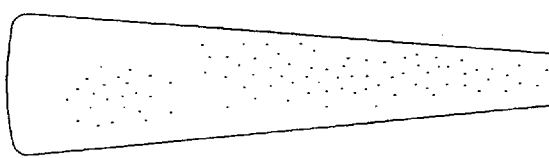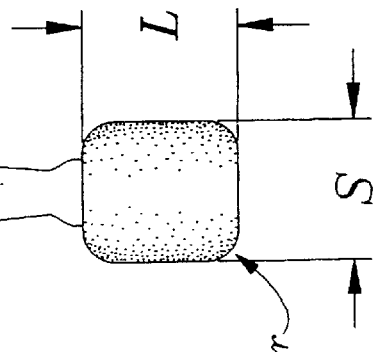

GRAPH 1

GRAPH 2

GRAPH 3

ANATOMICAL ORIFICE SIZERS AND METHODS OF ORIFICE SIZING

RELATED APPLICATION

The present application claims priority under 35 U.S.C §119(e) to provisional application No. 60/117,258, filed on Jan. 26, 1999 under the same title.

FIELD OF THE INVENTION

The present invention relates generally to anatomical orifice sizers and, more particularly, to an orifice sizer that is optimally proportional to an associated prosthetic device such as a heart valve, and methods of use.

BACKGROUND OF THE INVENTION

Surgical heart valve replacement has been performed in human beings for many years. Most frequently, the procedures are utilized to replace mitral or aortic valves in patients who suffer from valvular heart disease.

The four valves separate each ventricle from its associated atrium, or from the ascending aorta (left ventricle) or pulmonary artery (right ventricle). After the valve excision, the annulus generally comprises a ledge extending into and defining the orifice between the respective chambers. Prosthetic valves may attach on the upstream or downstream sides of the annulus ledge, but outside of the ventricles to avoid interfering with the large contractions therein. Thus, for example, in the left ventricle a prosthetic valve is positioned on the inflow side of the mitral annulus (in the left atrium), or on the outflow side of the aortic annulus (in the ascending aorta).

The annuluses comprise dense fibrous rings attached either directly or indirectly to the atrial and ventricular muscle fibers. In a valve replacement operation, the damaged leaflets are excised and the annulus sculpted to receive a replacement valve. Ideally the annulus presents relatively healthy tissue that can be formed by the surgeon into a uniform ledge projecting into the orifice left by the removed valve. The time and spacial constraints imposed by surgery, however, often dictate that the shape of the resulting annulus is less than perfect for attachment of a sewing ring. Moreover, the annulus may be calcified as well as the leaflets and complete annular debridement, or removal of the hardened tissue, results in a larger orifice and less defined annulus ledge to which to attach the sewing ring. In short, the contours of the resulting annulus vary widely after the natural valve has been excised, and sizing is often problematic.

In general, prosthetic aortic valves comprise a cylindrical valve body having a blood flow passageway extending longitudinally therethrough, and a suture ring formed annularly thereabout. The suture ring comprises suture penetrable material or a series of suture passage apertures, to facilitate anastomosis of the suture ring to the adjacent surgically-prepared aortic annulus. Because of the tricuspid configuration of the endogenous aortic valve, the natural aortic root has a non-planar, multi-curvate configuration. To correspond to such anatomical configuration of the natural aortic root, some or all of the aortic prosthetic valves of the prior art have utilized suture rings that are of a generally non-planar, multi-curvate configuration.

Conventional placement of the valve is intra-annular, with the valve body deep within the narrowest portion of the annulus to enhance any seal effected by the sewing ring/suture combination and reduce the chance of perivalvular leakage. To enable placement of the valve deep within the annulus, the sewing ring is compressed against the rigid valve body to match the annulus diameter. However, placement of the valve within the natural orifice naturally reduces the resulting flow orifice because of the thickness of the prosthetic valve. Therefore, some surgeons prefer, or some patients indicate, a supra-annular placement. In this position, only the rigid mounting portion of the valve enters the annulus, with the compressible sewing ring seated above the annulus, thus permitting a larger valve (larger flow orifice) to be implanted.

The ultimate success of any valve placement procedure is dependent on a number of factors, including the correct sizing and placement of the prosthetic valve. In this regard, it is common practice to utilize a sizing obturator to determine the correct size of prosthetic valve for implantation. Such sizing obturators typically comprise a series of different-sized cylindrical members (sometimes color-coded for size identification) that are independently attachable to a handle, and which are insertable into the surgically-prepared valve annulus to determine the actual size of the annular opening. Sizing obturators of the prior art typically comprise a generally cylindrical obturator body having a flat annular flange extending therearound. The flat annular flange is typically advanced into abutment with, but does not actually seat or nest within, the non-planar, three-peaked anatomy of the natural aortic root, which defines the superior aspect of the aortic annulus.

Examples of aortic and mitral valve sizing obturators of the prior art include the True-Size™ Aortic Obturator-Model 1161 and the True-Size™ Mitral Obturator-Model 1162, Baxter Healthcare Corporation, CVS Heart Valve Therapy Division, 17221 Red Hill Ave., Irvine, Calif. 92614. When the appropriate sizer is found, the correspondingly sized valve is chosen for implantation. Valves are typically provided in a range of sizes denoting the external mounting diameter in millimeters. Valves are most commonly available in odd 2 mm increments between 21 and 31 mm in diameter.

Over the years, the art of sizing a patient's aortic and mitral tissue annulus in order to select the correct prosthetic valve size has been less than satisfactory, particularly in the aortic position. A number of surgeons have experienced the problem of using a manufacturer's sizer to determine the correct valve size only to find the selected valve is either too large or too small for the patient's annulus. This problem particularly applies to 19, 21 and 23 mm aortic valves. It is also related to the fact that surgeons need to be able to implant the smaller aortic valves in the supra annular or intra annular position.

In spite of ongoing advances in sizing techniques, there exists a need for a more accurate sizing regimen.

SUMMARY OF THE INVENTION

The present invention provides a cylindrical heart valve sizer having a diameter larger than the diameter of a valve mounting portion of a valve corresponding to the sizer. Preferably the diameter is between about 0.2 mm to 0.4 mm larger than the valve mounting portion, and more preferably about 0.3 mm larger than the valve mounting portion. The cylindrical heart valve sizer desirably has a length of between about 19 mm to 22 mm, and has edges rounded to a minimum 1 mm radius.

The present invention also contemplates a method of sizing an anatomical heart valve annulus, comprising:

providing a set of cylindrical sizers having varying diameters;

sequentially inserting at least two of the sizers through the annulus;

determining the push force needed to pass each sizer through the annulus;

selecting a valve corresponding to the sizer for which the measured push force is between about 150 and 300 grams.

The step of determining is desirably accomplished with a load tester at the same time as the step of inserting.

A kit of anatomical heart valve annulus sizers corresponding to a set of heart valves is also provided. The kit includes a set of cylindrical sizers having varying diameters, each of the sizer diameters being sized larger than a rigid mounting portion of the corresponding heart valve. Each of the sizer diameters is desirably between about 0.2 mm to 0.4 mm larger than the rigid mounting portion of the corresponding heart valve, and preferably about 0.3 mm larger. Each of the sizers may a length of between about 19 mm to 22 mm, and the edges of each of the sizers are preferably rounded to a minimum 1 mm radius.

BRIEF DESCRIPTION OF THE DRAWINGS

FIG. 2 is an elevational view of a standard aortic valve and various marked dimensions;

FIGS. 3a and 3b are schematic views of the aortic valve of FIG. 2 in its supra-annular and intra-annular positions, respectively, in a heart valve annulus;

FIG. 3c is a schematic view of a downsized aortic valve of FIG. 2 in its intra-annular placement position in a heart valve annulus;

FIG. 6 is a series of schematic views of the relative diameters of an aortic valve, an annulus, and a sizer of the present invention, in particular illustrating a preferred size relationship therebetween;

FIG. 7 is a series of schematic views of the relative diameters of a mitral valve, an annulus, and a sizer of the present invention, in particular illustrating a preferred size relationship therebetween;

FIGS. 10–12 are elevational views of three different sized valve sizers of the present invention.

DESCRIPTION OF THE PREFERRED EMBODIMENTS

The present invention involves heart valve annulus sizer design, including the size, shape, and ergonomics. Certain parameters have been optimized and using those designs, preferred sizing and valve implantation techniques are suggested. It should be understood that the various sizes and shapes described herein are exemplary only, and modifications may be made consistent with the design considerations as detailed below.

Valve Placement

Correct valve sizing calls for a good matching fit between the tissue annulus diameter and the valve mounting diameter. However, given the discussion above with respect to uneven annuluses and time and special constraints, the relationship between the rigid mounting portion diameter of the valve and the tissue annulus diameter becomes more significant. Therefore, an understanding of typical valve structure is necessary.

The mounting portion of the aortic and mitral valve is a rigid area, typically cylindrical, and in the implant position this diameter will not change due to suturing technique, or the condition of the patient's annulus. This rigidity is in contrast to the compliant sewing ring that takes up the remaining exterior surface profile of the valve. The present invention makes use of the constant relationship between the rigid mounting portion and the rigid sizer to improve sizing accuracy.

Figure 1A:
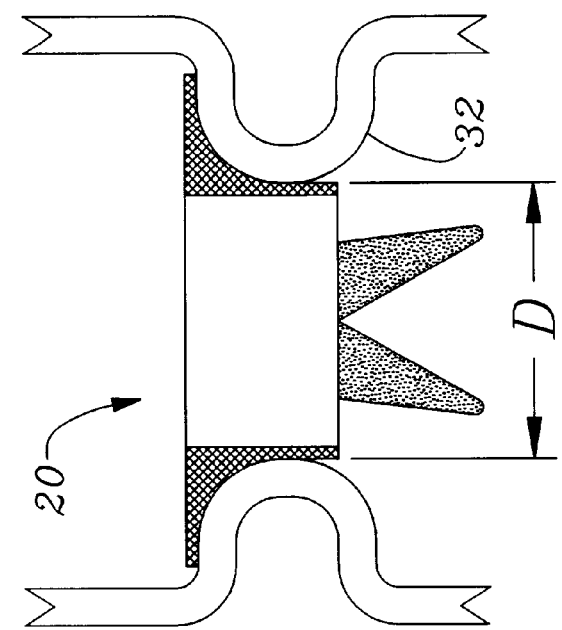
FIGS. 1a and 1b are schematic views of a mitral valve and its conventional placement position in a mitral annulus.
Figure 1B:
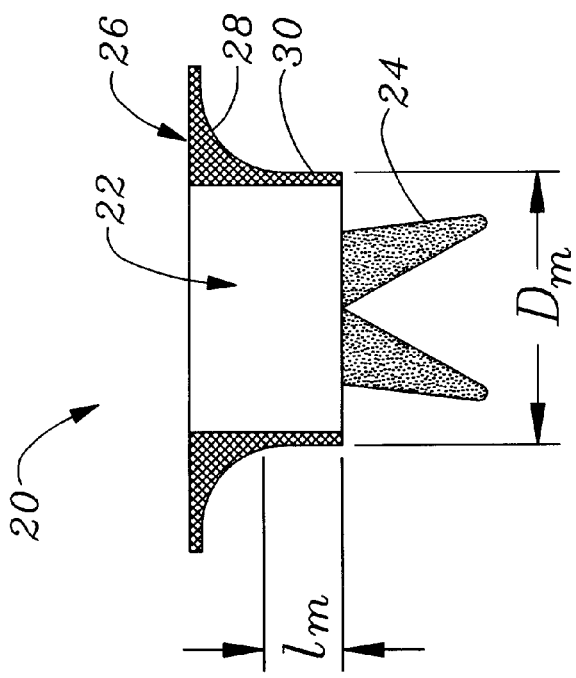

An exemplary mitral valve 20 is seen in FIG. 1a and comprises a rigid valve body 22 in which a plurality of leaflets 24 are mounted, and a sewing ring 26 extending outward therefrom. In the illustrated embodiment, the sewing ring 26 has an arcuate side 28 that is designed to better match and seal against the host annulus, although other sewing ring shapes can be used. Further, the valve 20 illustrated is a mechanical valve with rigid leaflets 24, but a similar structure could be present in a tissue valve. A rigid mounting portion 30 has a length $l_m$ of between about 2–4 mm, typically about 3 mm, and a diameter $D_m$ that varies between 19 and 33 mm depending on the valve size. In accordance with the present invention, correct sizing of the mitral annulus 32 involves matching this rigid mounting portion 30 of the valve 20 to the diameter D of the related portion of the tissue annulus, as seen in FIG. 1b.

An exemplary aortic valve 40 is seen in FIG. 2 and comprises a rigid valve body 42 in which a plurality of leaflets 44 are mounted, and a sewing ring 46 extending outward therefrom. A rigid mounting portion 50 has a length $l_m$ of between about 1–3 mm, typically about 1 mm, and a diameter $D_m$ that varies between 19 and 33 mm depending on the valve size.

In accordance with the present invention, correct sizing of the aortic annulus 52 for supra annular placement involves matching this rigid mounting portion 50 to the diameter D of the related portion of the tissue annulus, as seen in FIG. 3a. To implant a standard aortic valve 40 in the intra annular position however, the annulus ledge 52 is located on a plane 54 in the soft compliant portion of the sewing ring 46, as shown in FIG. 2. Matching a sizer to the valve diameter at this plane cannot be accurately gauged since there is no single fixed position for this mounting plane given the variables of surgeon preference, placement depth, annulus shape, sewing ring design, etc. In other words, the dimensions X and $D_m{'}$ in FIG. 2 vary considerably.

Figure 4:
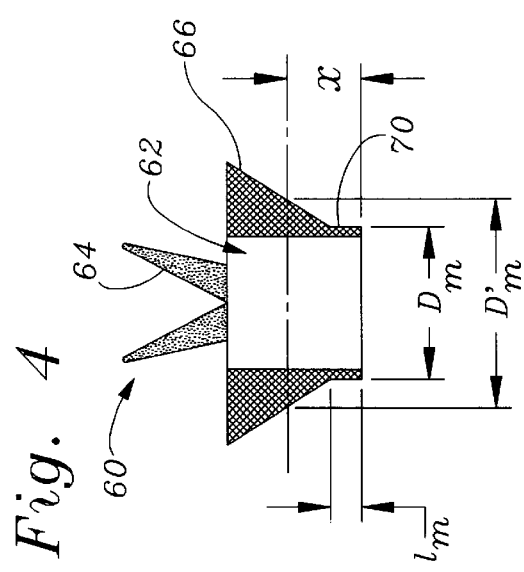
FIG. 4 is an elevational view of a non-standard aortic valve and various marked dimensions.

Another type of aortic valve 60 is seen in FIG. 4 and comprises a rigid valve body 62 in which a plurality of leaflets 64 are mounted, and a sewing ring 66 extending outward therefrom. The rigid mounting portion 70 has a length $l_m$ of between about 1–3 mm, typically about 2 mm, and a diameter $D_m$ that varies between 19 and 33 mm depending on the valve size. The length of the rigid mounting portion 70 of the valve 60 has been increased allowing it to seat lower down in the annulus. Such a valve may be obtained from the Baxter Healthcare of Irvine, Calif. under the product name MIRA Finesse mechanical valve, or from St. Jude Medical of Minneapolis, Minn. under the name HP mechanical valve. Again, the dimensions X and $D_m{}'$ for correct intra-annular placement vary considerably.

Figure 5A:
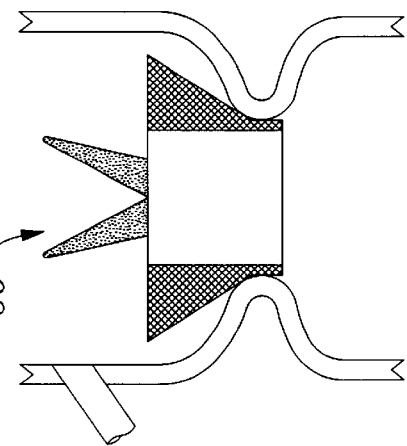
FIGS. 5a and 5b are schematic views of the aortic valve of FIG. 4 in its supra-annular and intra-annular positions, respectively, in a heart valve annulus.
Figure 5C:
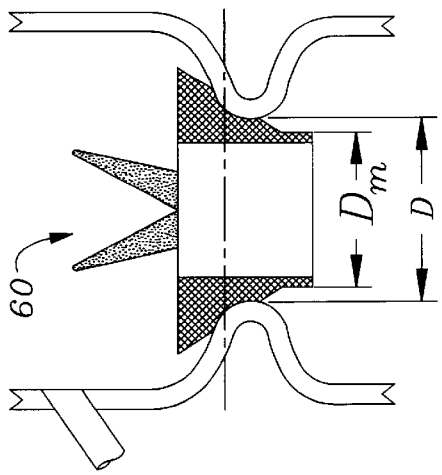
FIG. 5c is a schematic view of a downsized aortic valve of FIG. 4 in its intra-annular placement position in a heart valve annulus.
Figure 5B:
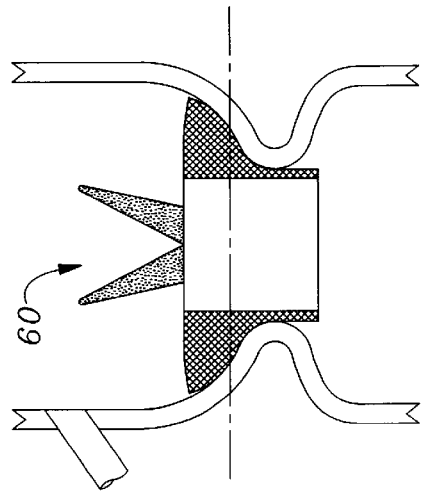

It will thus be understood that measuring the correct mounting diameter on a soft compliant sewing ring, such as seen at 46 in FIG. 2, is extremely inaccurate and subjective. In addition, the diameter of the tissue-contacting portion of the valve will change by an unknown amount in the intra-annular implant position since this position is achieved by manipulating the valve down into the annulus by a gentle pushing action, thereby slightly compressing the sewing ring and reducing its diameter. For instance, the compression for intra-annular placement is seen in FIGS. 3b and 5b. For these reasons current state of the art sizers cannot be used to directly select a standard aortic valve size that would guarantee accurate intra-annular placement.

If the surgeon does not wish to manipulate the valve down into the annulus, he/she can downsize the valve to allow the intra-annular placement without sewing ring compression. This is seen in FIGS. 3c and 5c, wherein the annulus diameter D is larger than the rigid valve mounting portion diameter $D_m$.

To minimize this inaccuracy, the present invention provides a method of assessing the aortic valve size required for intra-annular placement by first selecting the best sizer fit relative to the rigid mounting portion 46 of the valve. The surgeon then needs to determine the best method of using the valve size selected by the sizer, to facilitate intra annular placement. That is, the constant relationship between the rigid sizer selected and the rigid mounting portion 46 of the valve is used as a reference for valve selection depending on whether the valve will be implanted supra- or intra-annularly.

After finding the right sizer, which translates into knowledge of the correct diameter of the rigid mounting portion, as explained below, the surgeon has the choice of the following options.

1. The sizer selected standard aortic valve may be manipulated down into the annulus such as seen in FIGS. 3b and 5b. The surgeon's suturing technique, particularly if pledgets are used, the softness or compliance of the valve's sewing ring, and the tissue annulus compliance, will determine if this option is suitable for the patient involved.

2. The surgeon may select a valve model better suited to seat in the annulus in the intra annular position, where the length of the rigid mounting diameter portion of the valve has been increased allowing it to seat lower down in the annulus.

3. The surgeon can choose to downsize (or upsize) the valve size (see FIGS. 3c and 5c). That is, the valve mounting portion diameter $D_m$ is less than the annulus diameter D. The surgeon's suturing technique, particularly if pledgets are used, the softness or compliance of the valve's sewing ring, and the tissue annulus compliance, will determine if this option is suitable for the patient involved.

4. For 23 mm aortic valves and above, intra annular placement necessarily involves downsizing, see FIGS. 3c and 5c, if models more suitable for intra annular placement (e.g. MIRA Finesse mechanical valve) may not be available.

5. Some surgeons, based on experience, may know that their technique does change the diameter of the annulus after sizing and routinely compensate by downsizing or upsizing, relative to the size designated by the selected sizer.

6. For both supra annular and intra annular placement, if the sized annulus diameter is likely to change due to the surgeon's suturing technique, particularly if pledgets are used, then resizing after the sutures and pledgets are in place is recommnended.

Sizing Techniques

Valve sizing requirements really fall into two separate categories, sizing the tissue annulus diameter and also sizing to determine the acceptability of the seated valve in the annulus. These different requirements necessitate different sizer considerations. The following parameters/preferences were developed as a part of the present invention.

A. Sizing the Tissue Annulus Diameter

1. Shape

The surgeon is basically looking for is a light resistance "feel" when he pushes the sizer through the tissue annulus. Any sizer design incorporating shaped sections extending beyond the cylinder e.g. a lip or profile shape design, would tend to contact adjoining areas above or below the annulus, adding to the push force as the sizer travels through the annulus. This additional contact would adversely affect the accuracy of the push force and would no longer represent the true sizing "feel". In addition the push force would also suddenly change as the sizer lip or profile section bottomed out on the annulus making the "feel" assessment more difficult.

To push a sizer through the tissue annulus requires the sizer profile to be a plain cylinder and not a shaped profile. The "feel" is created by the push force required to pass the sizer through the tissue annulus that in turn is directly related to the diameter of the sizer cylinder and the diameter of the tissue annulus. The sizer that produces the correct "feel" identifies the proper valve size. The surgeon would then expect the selected valve mounting diameter portion of the selected valve to match the tissue annulus diameter as shown in FIGS. 1b, 3a and 5a.

Examples of sizing to ensure proper "feel" for aortic and mitral valves are illustrated in FIGS. 6 and 7. In these illustrations, the annulus diameter is D, the sizer diameter is S, and the "feel" dimension is given as A.

2. Diameter/finish.

In order to produce the desired light push force, the diameter of the sizer cylinder should always be larger than the mounting diameter portion of the corresponding valve. If the sizer cylinder was the same diameter, the desired light push force would not be achieved since the resultant push force would tend to be zero. This would lead the surgeon into believing that the sizer was too small. The next largest sizer would most likely be selected. This in turn would select a valve too large for the annulus. This would be totally unacceptable to the surgeon and this major issue must be avoided. A polished surface finish on this diameter is also required to ensure the sizer travels through the annulus smoothly.

3. Length.

The sizer cylinder must have sufficient length to provide the surgeon with adequate time to assess the "feel" before the sizer completely passes through the annulus. It must not be too long such that it makes frictional contact with other adjacent areas below the annulus as it passes through. It must not be too short that it passes through the annulus before the surgeon has time to assess the "feel".

4. Edges

The edges of the cylinder rims must be adequately rounded to ensure the sizer enters and exits the annulus smoothly and the passage through the annulus is not inhibited by the tissue "snagging" around a sharp-cornered rim edge.

5. Material

The sizer must be made from a clear transparent material to provide good visualization as it passes through the annulus.

6. Autoclaving

The sizer must be able to accommodate multiple autoclaving to facilitate reuse.

7. Accuracy

The selected sizer must indicate a valve size that produces a matching fit between the rigid mounting diameter portion of the valve and the tissue annulus. Note that this will only be achieved if the sized annulus diameter does not change after sizing.

The present study established specific values for some of these features in order to meet the "feel" requirements. These are detailed below, and as far as can be determined no commercially available sizers currently meet all of these requirements, and no similar sizing studies appear to have been conducted to date.

B. Tissue Annulus Seating Requirements

Figure 8:
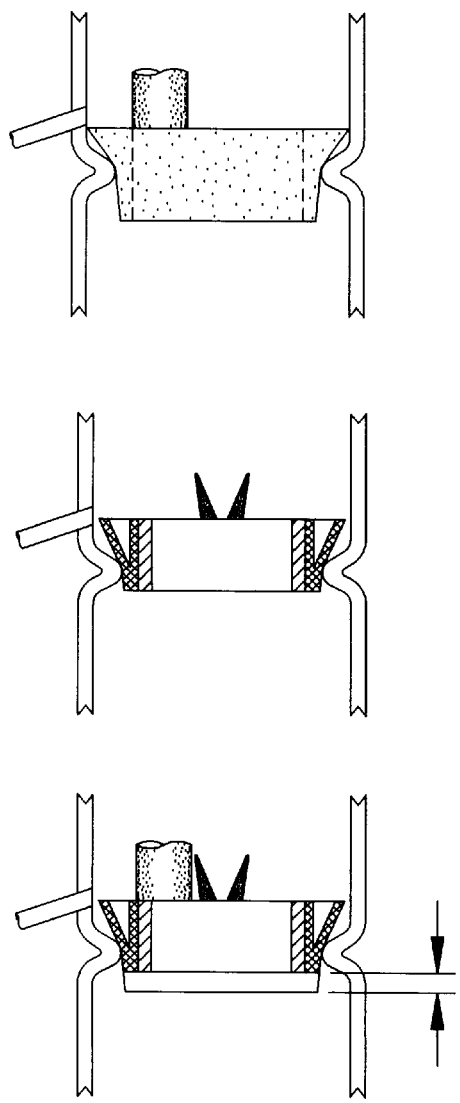
FIG. 8 is a series of schematic views of an optional sizing procedure to check the seating acceptability of an aortic valve.
Figure 9:
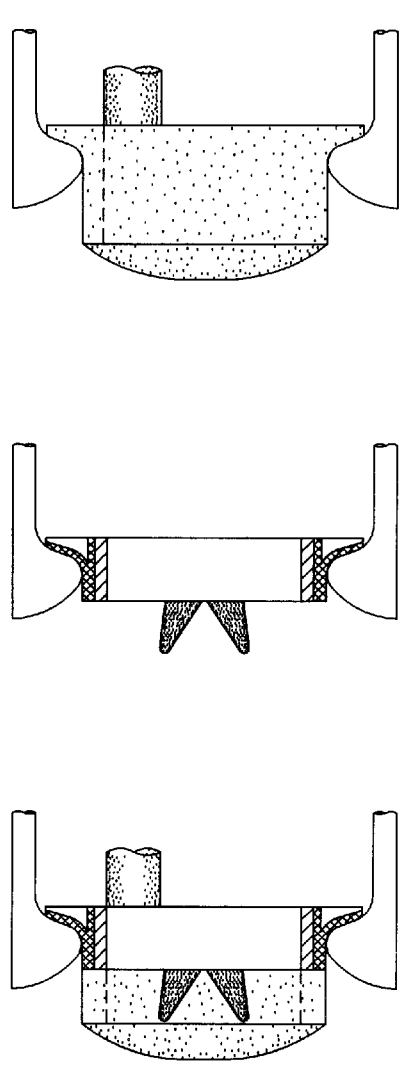
FIG. 9 is a series of schematic views of an optional sizing procedure to check the seating acceptability of a mitral valve.

In addition to determining the correct valve diameter some surgeons also like to verify that the valve seats correctly in the annulus. This requires the use of a shaped or profile sizer that preferably mimics the shape of the valve. The mitral shaped sizer should also be extended in length to represent the area taken up by the leaflets when they open and close. This checks that the leaflet motion will not be inhibited by chordae etc. Examples of sizing to ensure good valve seating for aortic and mitral valves are illustrated in FIGS. 8 and 9.

Sizer Design—Surgical Technique Considerations

In addition to establishing more accurate sizer design requirements, it has been found that surgical techniques and the condition of the annulus also tend to affect sizing, particularly in the small aortic valve sizes (19, 21 and 23 mm). A survey of a number of actively-practicing cardiac surgeons showed four different suturing techniques were being used, each technique having some or no affect on annulus diameter after sizing. Again it should be noted that the sizer can only be designed to accurately measure the tissue annulus diameter and match it to the rigid mounting diameter portion of the valve. Matching to any other portion of the valve renders the result totally subjective and unreliable. If the surgeon feels that his suturing technique is likely to change the initial sized annulus diameter, particularly if it involves the use of pledgets, then resizing after suturing is recommended.

Survey Methods.

To confirm some of the hypotheses of sizer design as detailed above, an in-depth study into the nature of valve annulus sizing and subsequent prosthetic valve selection was performed. As a part of the study, a survey of actively-practicing cardiac surgeons was completed in order to establish more detailed information on the surgeon's requirements relative to mechanical valve sizing and placement. Results of the study are as follows:

An initial survey was done with 19 European surgeons, experienced in mechanical valve implants. A 21 mm silicone rubber annulus (50 shore hardness to simulate a calcified annulus) was created and then sized by the surgeons by selecting one of 10 randomly identified cylinder shape sizers having the configuration as shown in FIG. 10. The 12 sizers were made with the cylinder diameters S increasing progressively from 19 mm to 23.6 mm in 0.2 or 0.5 mm steps with the dimensions called out in FIG. 10 provided below in TABLE I.

For the 21 mm annulus, two sizer sets were made where one set had a cylinder length L (FIG. 10) of 12 mm and the second set was 19 mm long. Each surgeon independently selected which one of the 12 randomly labeled sizers produced the feel force they required. Their expectation would be that this feel force would relate, in this case, to a valve sizer appropriate for a 21 mm annulus orifice. Each surgeon also confirmed that the model annulus was a correct match for the mounting diameter portion of the 21 mm aortic valve associated with this survey. Actually, the model annulus and demonstration valve used in the survey had an annulus diameter and a mounting diameter, respectively, of 20.9 mm. In addition, the model annulus was slightly out of round.

Separate from the surgeon experiments, an Instron tester incorporating a load cell was used to determine the push force required to pass each sizer through its related simulated annulus. The push force was applied manually after setting up the annulus on the load cell fixture. Both the annulus and each sizer were lubricated with diluted detergent solution during the Instron testing and the surgeon survey.

Of course, if practical, a load sensor may be used in conjunction with commercial sizers to give more precise and repeatable measures of the push force. Alternatively, the desirable push force results provided herein can be communicated to the surgeons in conjunction with training to incorporate into their technique in using the preferred sizers.

TABLE I

Dimensions of 21 mm Sizer set (Shore Hardness - 50)

| Sizer # | "S" Dia. + −.002 (in) | "S" Dia. + −.05 (mm) |
|---|---|---|
| 1 | .750 | 19.04 |
| 6 | .772 | 19.59 |
| 8 | .791 | 20.09 |
| 4 | .812 | 20.61 |
| 12 | .820 | 20.81 |
| 9 | .830 | 21.08 |
| 11 | .840 | 21.33 |
| 2 | .853 | 21.66 |
| 7 | .871 | 22.12 |
| 5 | .891 | 22.62 |
| 3 | .912 | 23.16 |
| 10 | .931 | 23.64 |

Two additional sets of data were obtained from surveys conducted with 25 mm and 29 mm simulated aortic annuluses and corresponding sets of sizers shown in FIGS. 11 and 12, with the corresponding dimensions provided in TABLES II and III below. It was agreed that the survey with the 21 mm, 25 mm and 29 mm annulus models would be sufficient to represent the entire product size range.

TABLE II

Dimensions of 25 mm Sizer set (Shore Hardness - 50)

| Sizer # | "S" Dia. + −.002 (in) | "S" Dia. + −.05 (mm) |
|---|---|---|
| 1 | .940 | 23.86 |
| 6 | .952 | 24.16 |
| 8 | .983 | 24.95 |
| 4 | .995 | 25.25 |
| 9 | 1.008 | 25.58 |
| 2 | 1.019 | 25.87 |
| 7 | 1.031 | 26.16 |
| 5 | 1.043 | 26.47 |
| 3 | 1.054 | 26.74 |
| 10 | 1.065 | 27.04 |
| 11 | 1.078 | 27.37 |

TABLE II-continued

Dimensions of 25 mm Sizer set (Shore Hardness - 50)

| Sizer # | "S" Dia. + −.002 (in) | "S" Dia. + −.05 (mm) |
|---|---|---|
| 12 | 1.089 | 27.65 |
| 13 | 1.102 | 27.96 |

TABLE III

Dimensions of 29 mm Sizer set (Shore Hardness - 50)

| Sizer # | "S" Dia. + −.002 (in) | "S" Dia. + −.05 (mm) |
|---|---|---|
| 1 | 1.145 | 29.06 |
| 6 | 1.157 | 29.37 |
| 8 | 1.169 | 29.66 |
| 4 | 1.179 | 29.92 |
| 9 | 1.193 | 30.29 |
| 2 | 1.206 | 30.60 |
| 7 | 1.217 | 30.89 |
| 5 | 1.228 | 31.16 |
| 3 | 1.240 | 31.47 |
| 10 | 1.252 | 31.79 |
| 11 | 1.265 | 32.10 |
| 12 | 1.276 | 32.40 |
| 13 | 1.288 | 32.69 |

Results (based on interviews)

1. During discussions all the surgeons confirmed that a plain cylinder-shaped sizer rather than a profile-shaped sizer (e.g. mimicking the entire valve profile) was preferred for sizing the tissue annulus. A profile-shaped sizer would only be useful if it was necessary to check the acceptability of the valve in the seated position.

2. All surgeons confirmed that a cylinder length of 19 mm was preferred compared to 12 mm. The longer cylinder length provided sufficient time to assess the feel as the sizer was pushed through the annulus. A longer length was not required and was undesirable. A shorter length e.g. 12 mm would not provide enough time to assess the "feel" or push force required. In addition a well rounded cylinder edge radius r was preferred to ensure a smooth insertion into the annulus could be accomplished.

Results (based on the functional surveys)

Figure 13:
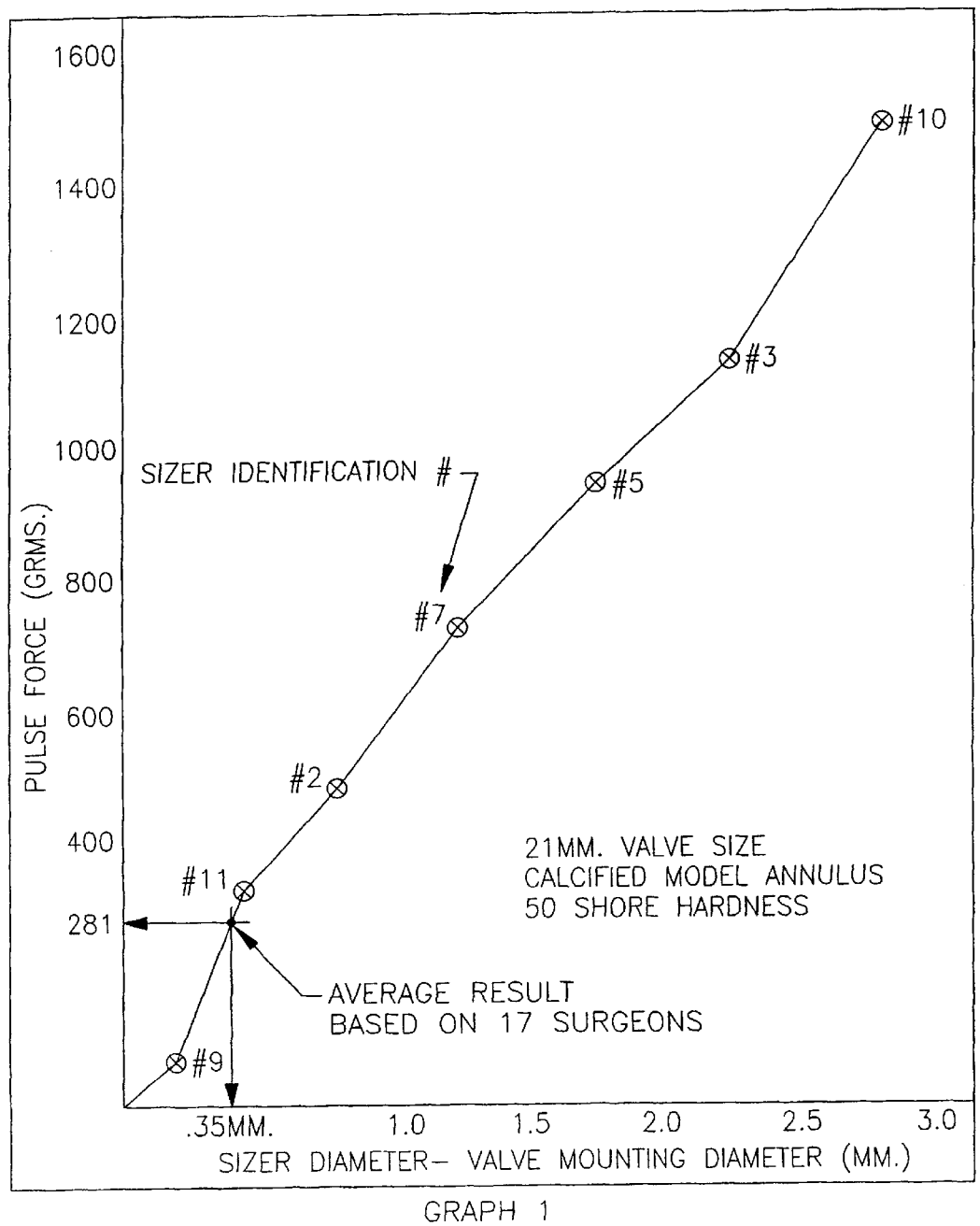
FIGS. 13–15 are graphs of the relationship between the diameter of various different sizers versus the measured force required to push each sizer through a particularly-sized simulated valve annulus, with the average preferred size/force selected by a panel of physicians indicated.
Figure 14:
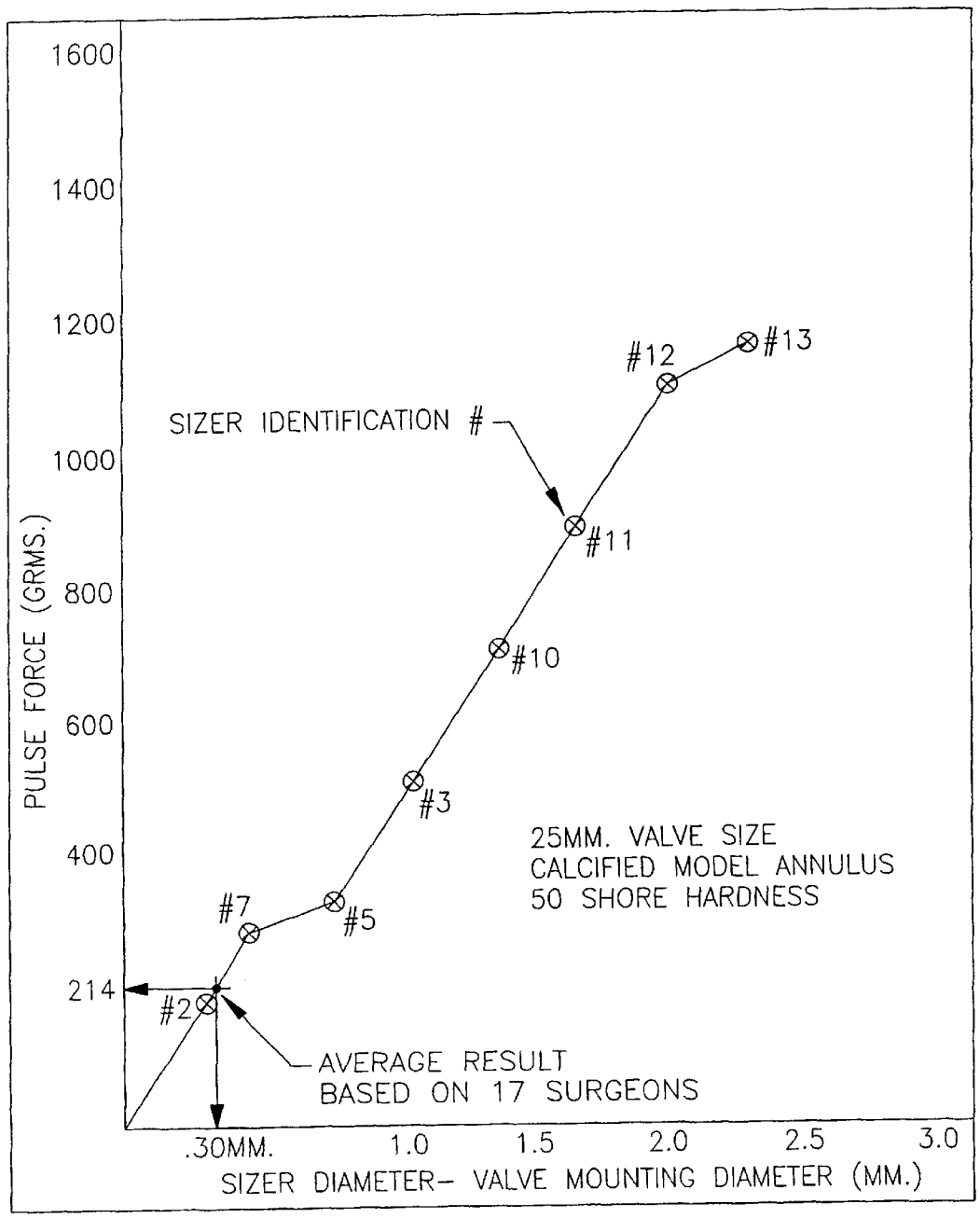
Figure 15:
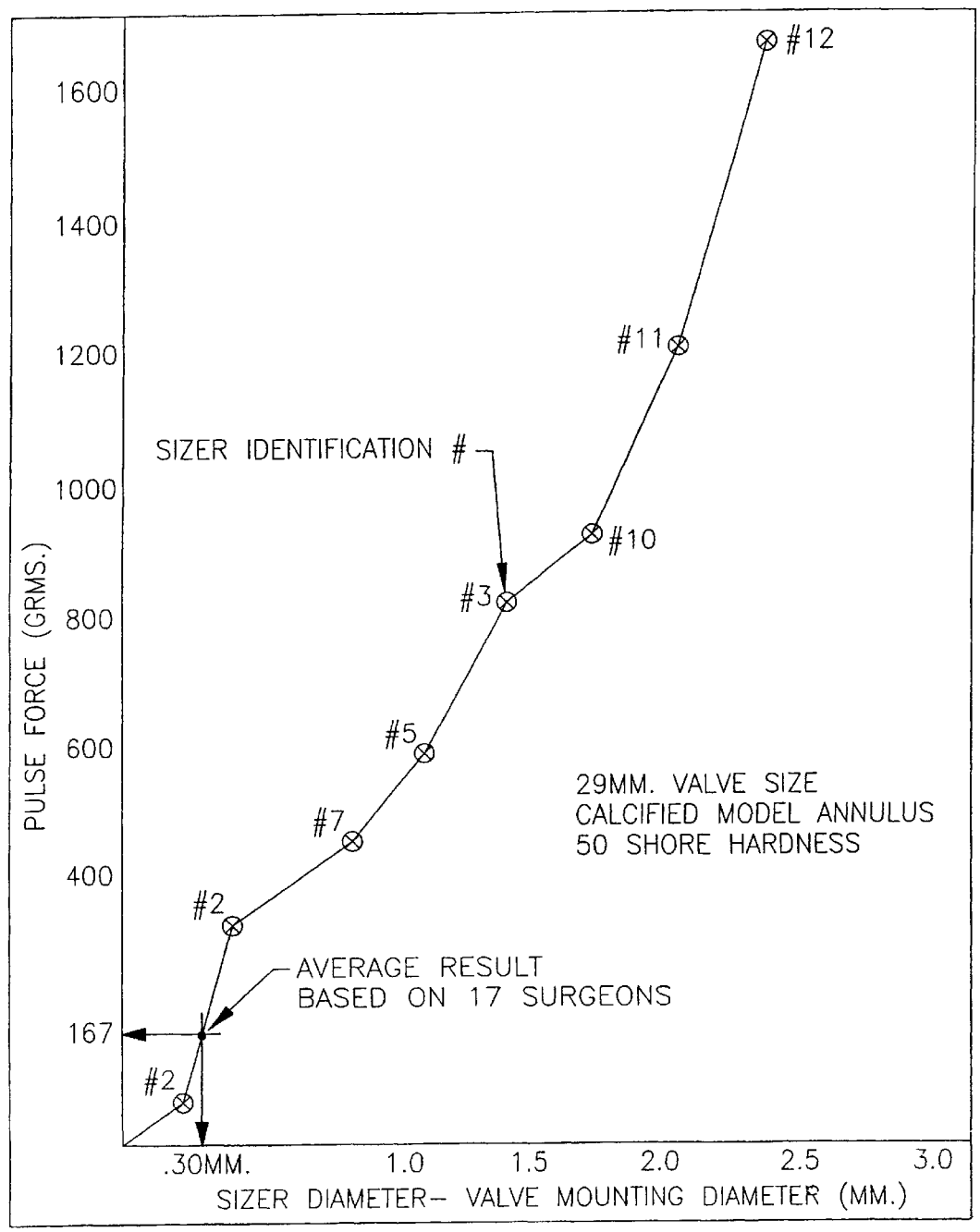

All the surgeons surveyed were experienced in valve replacement surgery. The 21 mm sizer survey included 19 different surgeons. The additional surveys for the 25 mm and 29 mm annulus models were done with 17 of the surgeons who participated in the initial 21 mm survey. The results were recorded in Tables IV, V and VI below. FIGS. 13, 14 and 15 show the results in graphical form.

TABLE IV 21 mm Sizing Survey

| Surgeon | Sizer # selected | Sizer Diameter (mm) | Push Force through simulated annulus (g) |
|---|---|---|---|
| #1 | 9 or 11 | 21.1 or 21.3 | 225 or 325 |
| #2 | 9 or 11 | 21.1 or 21.3 | 225 or 325 |
| #3 | 9 | 21.1 | 225 |
| #4 | 4 | 20.6* | 30* |
| #5 | 2 | 21.7 | 480 |
| #6 | 9 | 21.1 | 225 |
| #7 | 9 | 21.1 | 225 |

TABLE IV-continued 21 mm Sizing Survey

| Surgeon | Sizer # selected | Sizer Diameter (mm) | Push Force through simulated annulus (g) |
|---|---|---|---|
| #8 | 9 | 21.1 | 225 |
| #9 | 9 | 21.1 | 225 |
| #10 | 9 | 21.1 | 225 |
| #11 | 9 | 21.1 | 225 |
| #12 | 9 | 21.1 | 225 |
| #13 | 9 | 21.1 | 225 |
| #14 | 9 | 21.1 | 225 |
| #15 | 9 | 21.1 | 225 |
| #16 | 9 | 21.1 | 225 |
| #17 | 9 | 21.1 | 225 |
| #18 | 5 | 22.6 | 944 |
| #19 | 2 or 9 | 21.7 or 21.1 | 480 or 57 |
| #20 | 9 | 21.1 | 225 |
| #21 | 9 | 21.1 | 225 |
| #22 | 9 | 21.1 | 225 |
| #23 | 9 | 21.1 | 225 |
| #24 | 9 or 11 | 21.1 or 21.3 | 225 or 325 |
| #25 | 9 or 11 | 21.1 or 21.3 | 225 or 325 |
| | | | Average = 266 |

TABLE V 25 mm Sizing Survey

| Surgeon | Sizer # selected | Sizer Diameter (mm) | Push Force through simulated annulus* (g) |
|---|---|---|---|
| #1 | 7 | 26.1 | 272 |
| #2 | 2 | 25.9 | 179 |
| #3 | 2 | 25.9 | 179 |
| #4 | 2 | 25.9 | 179 |
| #5 | 2 | 25.9 | 179 |
| #6 | 7 | 26.1 | 272 |
| #7 | 2 | 25.9 | 179 |
| #8 | 7 | 26.1 | 272 |
| #9 | 2 | 25.9 | 179 |
| #10 | 2 or 7 | 25.9 or 26.1 | 179 or 272 |
| #11 | 2 or 7 | 25.9 or 26.1 | 179 or 272 |
| #12 | 2 or 7 | 25.9 or 26.1 | 179 or 272 |
| #13 | 2 or 7 | 25.9 or 26.1 | 179 or 272 |
| #14 | 2 or 7 | 25.9 or 26.1 | 179 or 272 |
| #15 | 2 | 25.9 | 179 |
| #16 | 2 or 7 | 25.9 or 26.1 | 179 or 272 |
| #17 | 2 or 7 | 25.9 or 26.1 | 179 or 272 |
| | | Average = 26.0 | Average = 215 |

*simulated annulus diameter was 25.7 mm

TABLE VI 29 mm Sizing Survey

| Surgeon | Sizer # selected | Sizer Diameter (mm) | Push Force through simulated annulus* (g) |
|---|---|---|---|
| #1 | 9 | 30.3 | 84 |
| #2 | 9 | 30.3 | 84 |
| #3 | 9 | 30.3 | 84 |
| #4 | 2 | 30.6 | 315 |
| #5 | 9 | 30.3 | 84 |
| #6 | 7 | 30.9 | 447 |
| #7 | 2 | 30.6 | 315 |
| #8 | 9 | 30.3 | 84 |
| #9 | 9 | 30.3 | 84 |
| #10 | 9 | 30.3 | 84 |
| #11 | 2 or 9 | 30.6 or 30.2 | 315 or 84 |
| #12 | 2 or 9 | 30.6 or 30.2 | 315 or 84 |

TABLE VI-continued 29 mm Sizing Survey

| Surgeon | Sizer # selected | Sizer Diameter (mm) | Push Force through simulated annulus* (g) |
|---|---|---|---|
| #13 | 2 or 9 | 30.6 or 30.2 | 315 or 84 |
| #14 | 2 or 9 | 30.6 or 30.2 | 315 or 84 |
| #15 | 9 | 30.3 | 84 |
| #16 | 2 or 9 | 30.6 or 30.2 | 315 or 84 |
| #17 | 9 | 30.3 | 84 |
|  |  | Average = 30.4 | Average = 167 |

*simulated annulus diameter was 30.10 mm

The vast majority of the surgeons surveyed sought a very light sizer push force when sizing the 21 mm, 25 mm and 29 mm annulus models. The average push force was in the region of 150 to 300 g representing a very light "feel". This light push force was produced by a sizer cylinder diameter approximately 0.3 mm larger than the actual valve mounting diameter and proved to be reasonably consistent over the three annulus sizes used in the survey. Other sizing information was also noted during the survey as detailed later in this report.

Survey Conclusions:
1. A low sizer push force range best represents the "feel" fit desired for sizing the annulus. The value of this light push force should be a nominal 200 gms with a suitable range between 150 and 300 g. FIGS. 13, 14 and 15 demonstrate the sensitivity of the sizer "feel" or push force to the sizer cylinder diameter. The more the "feel" or push force deviates away from the desired 150 to 300 gm. range the more inaccurate the sizing result will be.
2. The relationship between the valve rigid mounting diameter and the sizer cylinder diameter is uniform through the size range. The sizer cylinder diameter should be a nominal 0.3 mm larger than the valve mounting diameter with a range of 0.2 mm to 0.4 mm.
3. The length of the cylinder should be a nominal 19 mm with a range of 19–22 mm.
4. The cylinder rim edges should be rounded by a 1 mm minimum radius (r in FIGS. 10–12).

Many commercially available sizer designs do not meet the features 1, 2, 3, or 4 listed above, which probably explains the less than satisfactory sizing performance experienced in the marketplace.

No papers dealing with in depth sizing studies appear to have been published, therefore surgeons may not necessarily realize exactly what is involved when sizing a tissue annulus. The expectations after sizing appears to be that the sizer should measure the tissue annulus and identify the related valve size to be selected and ensure that supra annular or intra annular placement can be achieved. For standard aortic valves this is only true for supra annular placement unless the valve is specifically designed for intra annular placement. This also assumes that the annulus diameter does not change after sizing due to suturing technique. This cannot be assumed. It should be noted that four different suturing techniques, including the use of pledgets, were currently being used by the participating surgeons and with two implant positions to accommodate, the annulus diameter, in some cases does change after sizing.

This study was done initially for a specific mechanical valve sizer, however, this information may also be applicable to other mechanical valve sizers and to sizers for tissue valves.

It is understood that the examples and embodiments described herein and shown in the drawings represent only the presently preferred embodiments of the invention, and are not intended to exhaustively describe in detail all possible embodiments in which the invention may take physical form. Indeed, various modifications and additions may be made to such embodiments without departing from the spirit and scope of the invention.

What is claimed is:

1. A method of sizing an anatomical heart valve annulus, comprising:

providing a set of cylindrical sizers having varying diameters;

sequentially inserting at least two of the sizers through the annulus;

determining the push force needed to pass each sizer through the annulus;

selecting a valve corresponding to the sizer for which the measured push force is between about 150 and 300 grams; wherein the step of determining is accomplished with a load sensor.

2. The method of claim 1, wherein the step of determining is accomplished at the same time as the step of inserting.

* * * * *